United States Patent
Wortmann et al.

(10) Patent No.: US 12,064,292 B2
(45) Date of Patent: *Aug. 20, 2024

(54) CRANIAL IMMOBILIZATION SYSTEM

(71) Applicant: Brainlab AG, Munich (DE)

(72) Inventors: Manuel Wortmann, Munich (DE); Andreas Bereket, Munich (DE)

(73) Assignee: Brainlab AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/442,459

(22) Filed: Feb. 15, 2024

(65) Prior Publication Data

US 2024/0189059 A1    Jun. 13, 2024

Related U.S. Application Data

(63) Continuation of application No. 18/128,024, filed on Mar. 29, 2023, now Pat. No. 11,937,985, which is a
(Continued)

(51) Int. Cl.
*A61B 90/18* (2016.01)
*A61B 90/14* (2016.01)
(Continued)

(52) U.S. Cl.
CPC .............. *A61B 90/18* (2016.02); *A61B 90/14* (2016.02); *A61B 6/0421* (2013.01); *A61B 2090/101* (2016.02); *A61N 2005/1097* (2013.01)

(58) Field of Classification Search
CPC .............. A61B 90/10; A61B 90/14–18; A61B 2090/101; A61B 6/04; A61B 6/0407;
(Continued)

(56) References Cited

U.S. PATENT DOCUMENTS 5,370,117 A    12/1994   McLaurin, Jr.
5,377,510 A *  1/1995    Smith .................. E05B 35/008
                                                        128/878
(Continued)

FOREIGN PATENT DOCUMENTS

CN    104822322 A    5/2015
CN    105555197 A    5/2016
(Continued)

OTHER PUBLICATIONS

European Patent Office, International Search report and Written Opinion for corresponding PCT/EP2017/059420, date of mailing Dec. 6, 2017, pp. 1-13.
(Continued)

*Primary Examiner* — Michelle J Lee
(74) *Attorney, Agent, or Firm* — Tucker Ellis LLP

(57) ABSTRACT

A head immobilization system for immobilizing a patient's head in a supine position of the patient includes a support rail structure adapted to be coupled to a patient rest. The system can further include a mask frame adapted to be coupled to at least one deformable upper mask sheet. The mask frame is releasably connected to the support rail structure via a first interface section and a second interface section, with at least two pins protruding from the first interface section in a first direction, and at least two pin-receptions provided at the second interface section. Each one of the pin-receptions receives one of the pins. A catch-mechanism for each pin-reception and each corresponding pin allows the pin to be pushed further into the pin-reception in the first direction, but interlocks in case of an attempted withdrawal of the pin from the pin-reception in a second, opposite direction.

14 Claims, 4 Drawing Sheets

Related U.S. Application Data continuation of application No. 17/665,666, filed on Feb. 7, 2022, now Pat. No. 11,642,190, which is a continuation of application No. 15/759,690, filed as application No. PCT/EP2017/059420 on Apr. 20, 2017, now Pat. No. 11,278,368.

(51) Int. Cl.
*A61B 6/04* (2006.01)
*A61B 90/10* (2016.01)
*A61N 5/10* (2006.01)

(58) Field of Classification Search
CPC ... A61B 6/0421; A61B 6/0428; A61B 6/0492; A61N 2005/1092; A61N 2005/1097; A61F 5/37; A61F 5/3707; Y10T 403/32; Y10T 403/32254; Y10T 403/32426–32451; Y10T 403/32467–32483; Y10T 403/32524; A61G 13/10; A61G 13/12–121; A61G 13/1295; A61G 7/05; A61G 7/065–072
See application file for complete search history.

(56) References Cited

U.S. PATENT DOCUMENTS

| | | | |
|---|---|---|---|
| 5,680,989 A | 10/1997 | Plachy et al. | |
| 5,702,406 A | 12/1997 | Vismeier et al. | |
| 5,741,102 A * | 4/1998 | Everett | F16B 21/088 411/510 |
| 5,775,337 A | 7/1998 | Hauger et al. | |
| 5,848,449 A * | 12/1998 | Hauger | A61B 6/0421 5/601 |
| 6,083,528 A | 7/2000 | Elliesen et al. | |
| 6,412,633 B1 * | 7/2002 | Costa | E05B 73/0023 220/326 |
| 8,814,105 B2 * | 8/2014 | Azad | A47G 1/164 248/495 |
| 11,278,368 B2 | 3/2022 | Wortmann et al. | |
| 2002/0108616 A1 | 8/2002 | Woodburn, III | |
| 2015/0047652 A1 | 2/2015 | De Mooij | |
| 2016/0206395 A1 | 7/2016 | Coppens et al. | |

FOREIGN PATENT DOCUMENTS

| | | |
|---|---|---|
| CN | 105611968 A | 5/2016 |
| DE | 4432891 A1 | 3/1996 |
| EP | 1582187 A1 | 10/2005 |
| EP | 1694232 B1 | 8/2013 |
| FR | 2765487 A1 | 1/1999 |

OTHER PUBLICATIONS

Chinese Office Action and English translation for corresponding Chinese application No. 201780002938.9, dated Oct. 15, 2020, 8 pages.

* cited by examiner

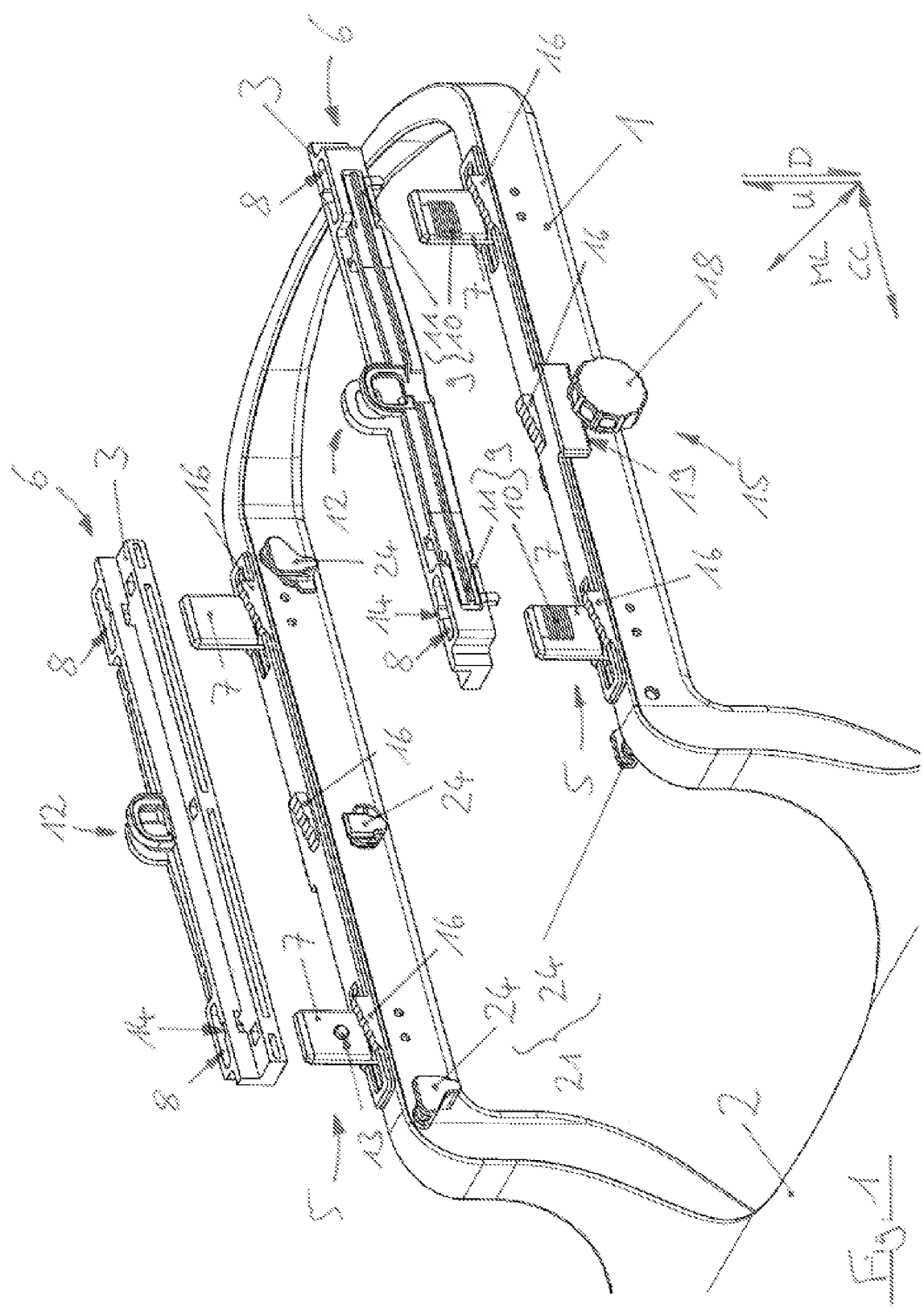

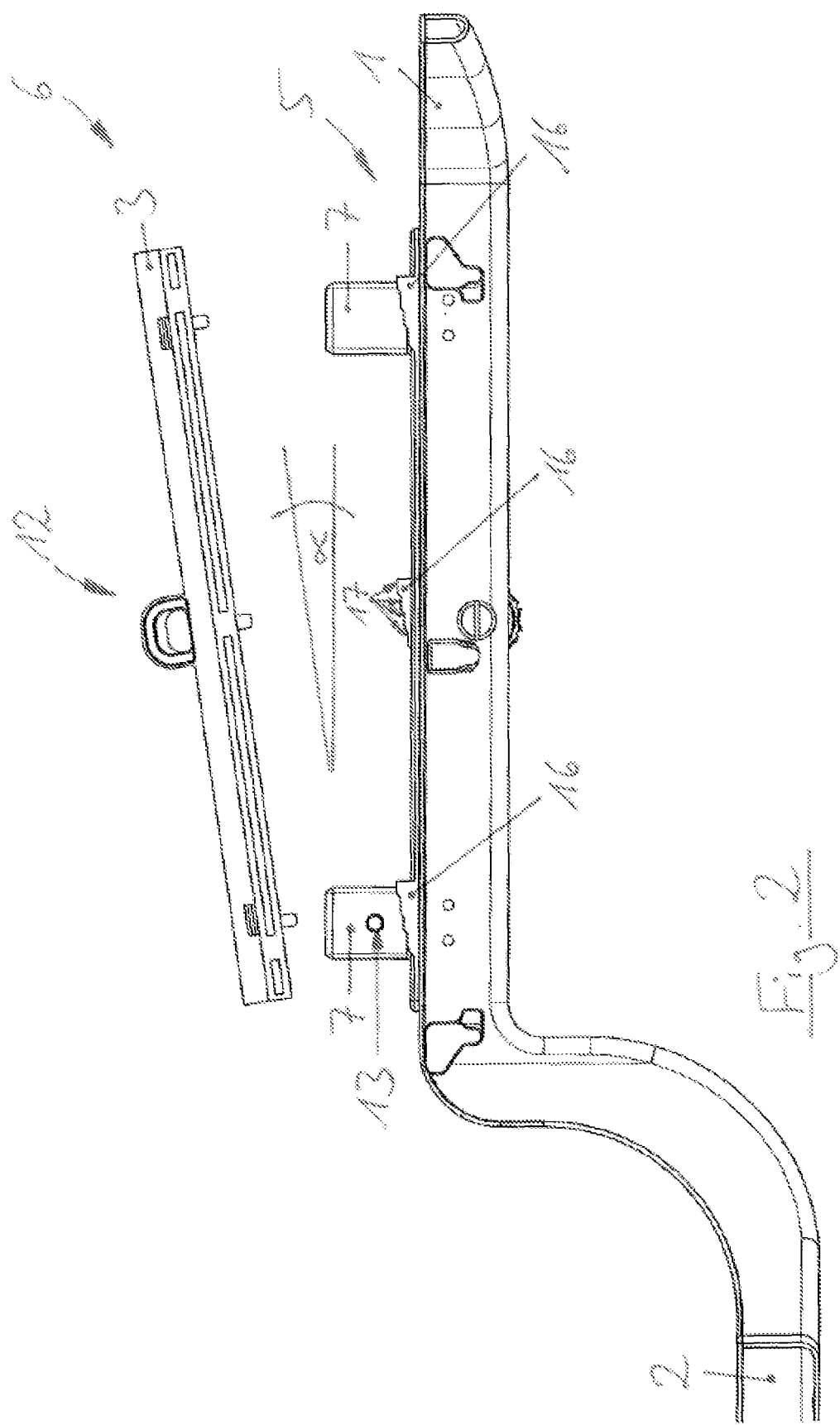

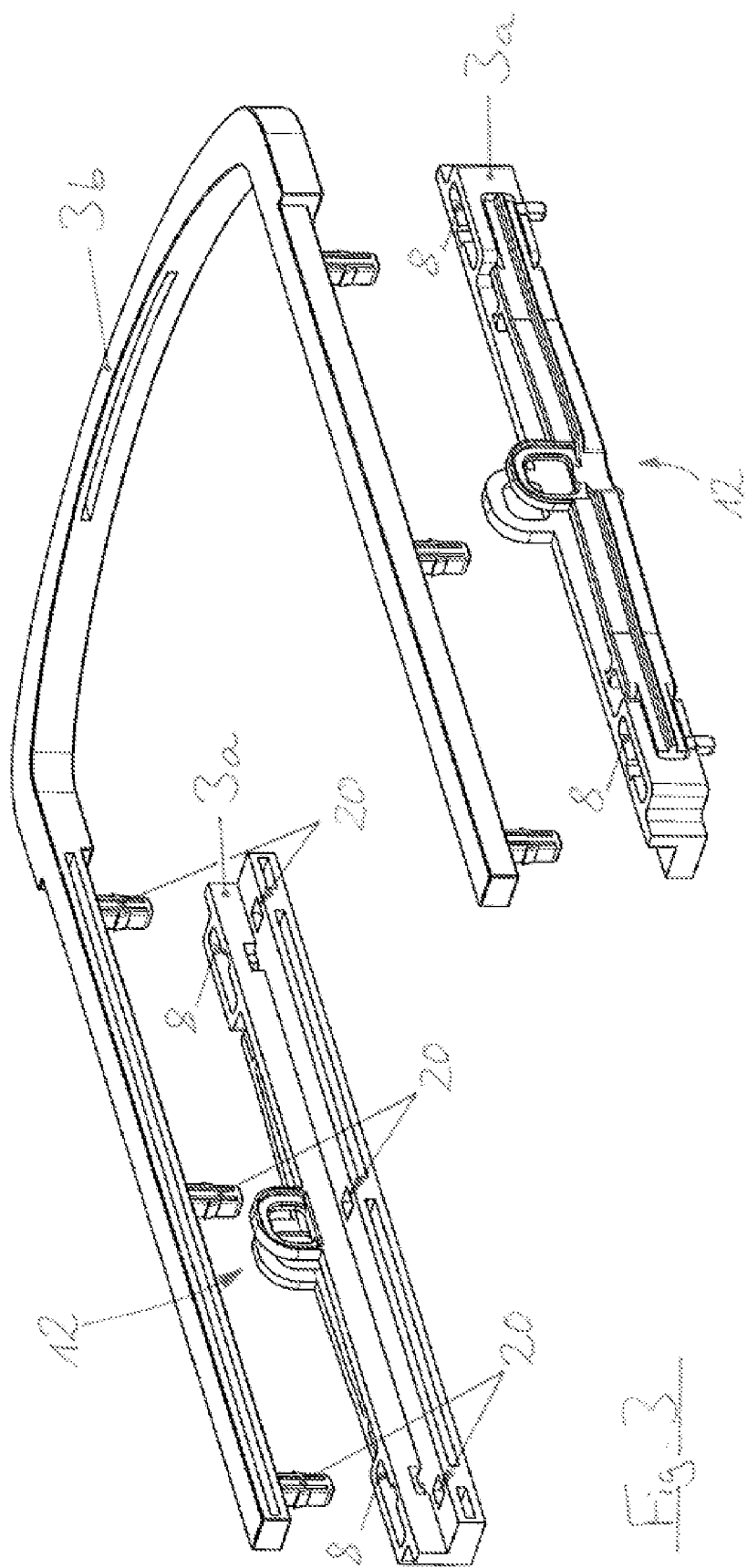

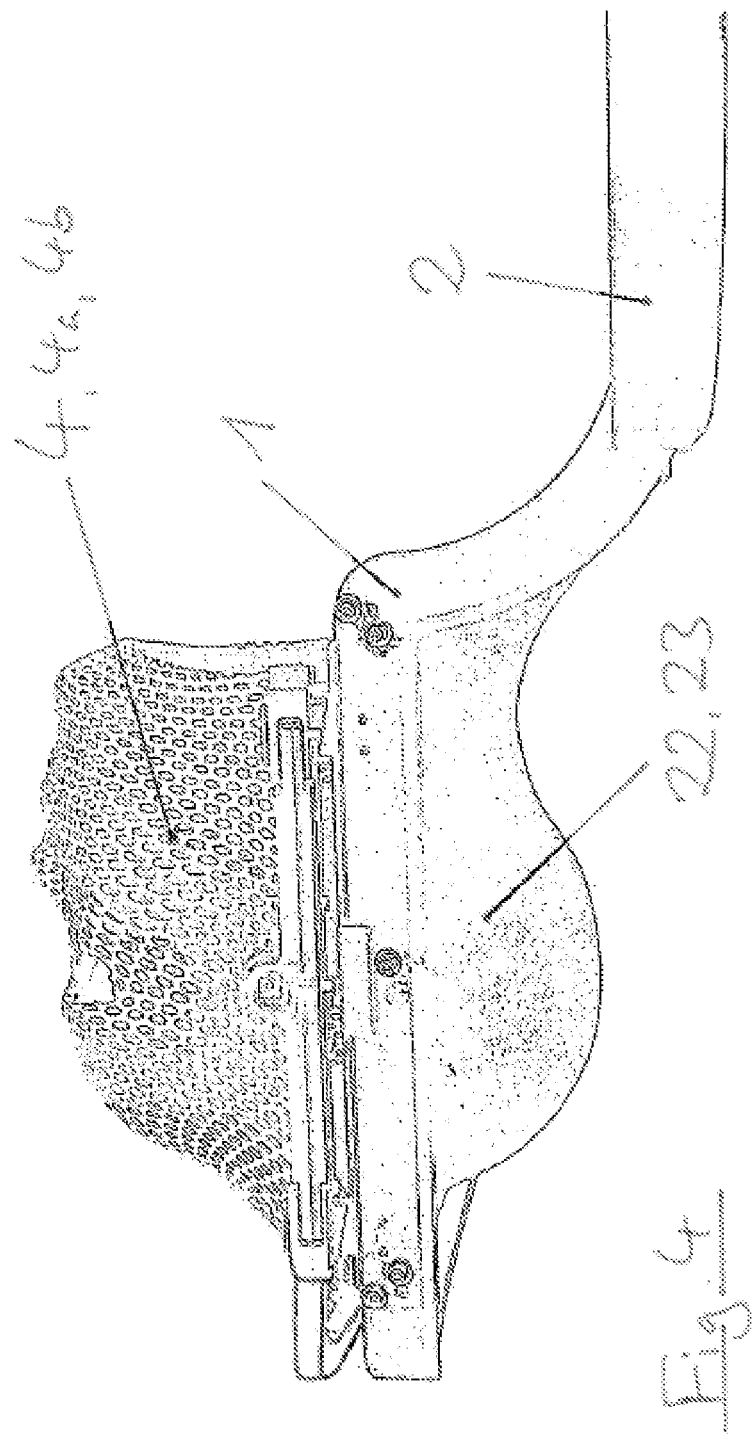

CRANIAL IMMOBILIZATION SYSTEM

RELATED APPLICATION DATA

This application is a continuation of U.S. application Ser. No. 18/128,024 filed Mar. 29, 2023, which is a continuation of U.S. application Ser. No. 17/665,666 filed Feb. 7, 2022, which is a continuation of U.S. application Ser. No. 15/759,690 filed Oct. 25, 2018, which is a national phase application of International Application No. PCT/EP2017/059420 filed Apr. 20, 2017, the entireties of which are incorporated herein by reference.

TECHNICAL FIELD

The present invention relates to an immobilization system for immobilizing the head of a patient by covering the head's surface at least partially with an immobilization mask. The present invention may be used for non-invasive patient immobilization and reproducible positioning during stereotactic radiosurgery and radiotherapy treatments.

SUMMARY

Immobilization masks are used for orthopedic applications as well as for therapeutic or diagnostic procedures, radiotherapy or diagnostic imaging, for which the head of a patient has to be immobilized relative to a fixed structure and to ensure a high reproducibility of the head's spatial position during the treatment or diagnostic procedure.

To immobilize a patient's head for radiation therapy or diagnostic imaging, the head is connected to a fixed supporting structure such as a patient bed in a spatially fixed arrangement, and therefore in a reproducible position relative to a radiation or imaging device. For this purpose, immobilization devices are known, for example from DE 44 32 891 A1 or US 2016/0206395 A1, which provide a rigid connection between the head and the supporting structure, wherein the head is held within a mask that has at least one sheet-like layer of a low temperature thermoplastic material, which previously has been individually adapted to the head in a heated condition so that, after the mask has cooled down and cured, the mask tightly fits to the head to be immobilized.

A problem of known systems is the amount of steps that are necessary to attach the mask to the patient and to adjust it to the patient's anatomy. This is time consuming and increases the possibility of handling errors.

A further problem is the characteristic of many materials that absorb at least part of the radiation emitted during radiation therapy or diagnostic imaging.

The present invention provides an immobilization mask system that is fast and easy to handle and that absorbs less radiation than known systems.

The system is defined by the appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The immobilization system according to the present invention comprises:
- a support rail structure adapted to be coupled to a patient rest and extending at least on both lateral sides of the patient's head,
- a mask frame adapted to be coupled to at least one deformable upper mask sheet, wherein the mask frame is releasably connected to the support rail structure via a first interface section and a second interface section, with at least two pins protruding from the first interface section in a first direction, and at least two pin-receptions provided at the second interface section, wherein each one of the pin-receptions receives one of the pins, and
- a catch-mechanism for each pin-reception and each corresponding pin, which allows the pin to be pushed further into the pin-reception in the first direction, but which interlocks in case of an attempted withdrawal of the pin from the pin-reception in a second, opposite direction.

A first basic component of the inventive system is formed by the support rail structure which can be releasably or permanently coupled to a patient rest, herein also referred to as "overlay board". The overlay board may be adapted to be used on CT-treatment tables and has therefore a flat design. It may comprise a flat carbon sandwich structure which supports the patient's body and shoulders, from which the support rail structure which may be also made from carbon protrudes and supports the patient's neck and head, and which may even extend the treatment table. In order to minimize the risk of collisions, the support rail structure may be located as close as possible to the patient's head. The support rail and the patient rest form a support for the patient's body, head and neck and hold them at a fixed position with respect to a CT-table or a treatment table as used during radiotherapy or radiosurgery. The support rail and the overlay board may be made from a radiolucent material, and further may be sized such that the rail and the board fit tightly around the patient which will reduce the risk of collisions with the gantry of an imaging or treatment apparatus. Further, the radiotherapy device may be a linear accelerator.

The mask frame is coupled to a thermoplastic mask that can be deformed so that it adapts to the anterior contour of a patient's head, for example including the forehead, nose, mouth and chin region. This mask may comprise more than one thermoplastic layer, wherein the layers may be molded to the head contour simultaneously or separately, wherein an optional moldable nose bridge may be provided, as well. In a specific example, the anterior thermoplastic mask contains two sheets of a thermoplastic material. The one or more plane mask sheets are molded to the head contour by heating them up until they reach a temperature at which they become flexible so that they can be molded to a desired contour. Each mask sheet consists of a thermoplastic sheet which may be framed on at least two sides by one or more rails of the mask frame.

Moreover, the inventive system comprises means which allow a quick fixation of the mask frame to the support rail structure. According to the invention these means comprise at least two pins which protrude from either the mask frame or the support rail structure, and at least two corresponding receptacles for these pins on the support rail structure or the mask frame, respectively. A catch-mechanism provided for each one of the pin-receptacle-pairings only allows the mask frame to be pushed towards the support rail structure, with the pins further entering the corresponding receptacles, but prevents an opposite movement of the mask frame away from the support rail structure, with the pins moving in the opposite direction within the receptions.

According to one embodiment of the present invention, the catch-mechanism comprises saw-toothing on the pin outside surface, which interlocks with corresponding saw-toothing on the inside surface of the pin-reception that is held resiliently with respect to the pin-reception, particularly wherein the saw-toothing of the pin-reception is spring loaded with respect to the pin reception.

In other words, the interlocking saw-toothings on the pin and in the pin-reception act as a one-directional ratchet, allowing the pins to move within the receptions in one direction only, thereby providing an automatic locking functionality.

According to another preferred embodiment, the catch-mechanism is operably connected to a release-mechanism for unlocking said interlock, particularly wherein a plurality of catch-mechanisms are operably connected to the same release-mechanism. Only by operating the release-mechanism, the interlock can be released or, more specifically, the two interlocking saw-toothings may be separated from each other, such that the mask frame can be removed from the support rail structure again. In a more specific example, the release-mechanism may comprise one or more levers, one section of which can be grasped by a person, whereas an opposed section causes a catch to release or "open". In an even more specific embodiment, the at least one lever may be rotatably connected to the mask frame via one or more film-joints, wherein one end of the lever is provided with the saw-toothing that interlocks with the saw-toothing of a pin. By moving the second end of the lever in a certain direction, the lever will rotate around the film-joint(s), such that the second end of the lever together with its saw-toothing will move away from the pin and its saw-toothing, thereby releasing the interlock.

According to another embodiment of the present invention, at least one of the pins, particularly the pins disposed at each one of the lateral sides of the patient's head in a most caudal position have a guidance protrusion that engages into a corresponding notch formed in the pin-reception. Additionally or alternatively, the dimensions of the pin-receptions in the cranial-caudal direction are sized (i.e. "wider") to allow the pins to enter the pin-receptions even with the mask frame being tilted up to a predetermined angle with respect to the support rail structure and around a medial-lateral direction.

This provides a certain degree of freedom when the mask frame together with the mask is pushed onto the support rail structure, thereby causing the mask to firstly adapt to the contour of the patient's chin. This is because it is often not desired to "push" mask layers onto the patient's forehead in a single anterior-posterior motion, but rather to "tilt" the mask when it is pushed onto the patient's face, starting with the chin-portion of the mask being pushed onto the patient's chin.

As already described further above, the inventive system is preferably designed to avoid collisions with a gantry surrounding the patient and the patient table during treatment. Therefore, the support rail structure may extend, particularly within a frontal plane of the patient in the supine position, cranially around a close proximity to the patient's head.

Further, the first interface section, provided at the support rail structure or the mask frame, or the second interface section, provided at the mask frame or the support rail structure, respectively, may comprise at least one adjustable stop-mechanism, particularly one adjustable stop-mechanism on each one of the lateral sides of the patient's head, that limits the distance by which the pins can be pushed into the pin-receptions in the first direction by which the mask frame can be pushed towards the support rail structure.

In other words, at least one of the interface sections may comprise a physical limiter on which the respective other interface comes to rest in a final position of the mask frame with respect to the support rail structure. Thus, the mask frame and the mask are prevented from being pushed further towards the support rail structure and the patient's forehead beyond a predefined limit.

According to a specific embodiment of the inventive system the at least one stop-mechanism comprises at least one section having stepped locating surfaces, and wherein the section is displaceable with respect to the pins, particularly along the support rail structure in a cranial-caudal direction.

With a plurality of locating surfaces being provided at different heights on the interface, and being movable with respect to the interface, it becomes apparent that the distance at which the interfaces will come to rest with respect to each other can be adjusted by moving the section together with the locating surfaces formed thereon. As soon as a "higher" locating surface is replaced by a "lower" locating surface at a position at which a corresponding member of the other interface will come to rest, the interfaces are allowed to approach each other further. The other way round, replacing a "lower" locating surface by a "higher" locating surface at that position will cause the interfaces to come to rest with respect to each other at a more distant position.

For adjusting the stop-mechanism, particularly for moving or displacing the at least one section having the locating surfaces, the stop mechanism may comprise at least one adjustment member, particularly wheel, via which a person may adjust the stop-mechanism. In particular, the adjustment wheel may be connected to the at least one section having a plurality of locating surfaces via a rack and pinion drive.

While it is conceivable that the displaceable section having the locating surfaces is adapted to be shifted in a translatory motion with respect to one of the interfaces on the support rail structure or the mask frame, a rotatory motion or even a combined rotatory-translatory motion is conceivable just as well.

According to a further embodiment of the present invention, the mask frame comprises an engagement system comprising a first sub-frame adapted to be coupled to at least one first deformable upper mask sheet, and a second sub-frame adapted to be coupled to at least one second deformable upper mask sheet, wherein the first sub-frame is adapted to be connected to the second sub-frame in a detachable or a non-detachable manner, particularly via one or more detachable or non-detachable snap-in connections.

Such divided mask frame is in particular useful if more than one deformable mask-layer is used and it is desired to mold the layers onto the head contour separately. In such case, a first sub-frame can, in a first step, be attached to the support rail structure, wherein the one or more layers connected to the first sub-frame adapt(s) to the patient's head contour. After the first sub-frame has been put in place, the second sub-frame with one or more mask layers attached thereto can be installed in the same manner, except that it is connected to the support rail structure indirectly via the first sub-frame. In most cases, there is no need to separate the two sub-frames again after the masks have been molded, such that the two sub-frames may be connected to each other in a non-detachable manner. However, it is also conceivable that the two sub-frames may be adapted to be disconnected from each other again after the respective mask layers have been molded.

So far, mask layers have been described which are molded to the anterior head contour of the patient. The inventive system may however further comprise one or more similar mask layers provided for the posterior region of the head, which are adapted to be molded in a similar manner. Such "rear" masks may comprise a mask frame, as well, by which they can be held in place with respect to the support rail structure.

Additionally or alternatively to one or more deformable mask sheets for the posterior region of the patient's head, a posterior head support may be provided which can be connected to the support rail structure to provide support for the patient's head when it is immobilized by the inventive system. Such head support may comprise a formed sheet that is shaped to ergonomically accommodate the patient's rear head. Thus, the head support may also be used as a mold for molding one or more rear mask layers. For example, the head support that has a depression to accommodate the patient's head is connected to the support rail structure, and one or more heated and therefore deformable rear mask layers are arranged above that depression and are also connected to the rail support structure. After that, the patient's head is lowered onto the head support, wherein the rear mask layers are forced into a shape that is defined by the depression within the head support and the posterior region of the patient's head. After the thermoplastic material has cured again, the new shape of the rear masks is permanent such that the rear masks can serve as a head-support for later procedures.

For attaching the head support and/or a frame for one more rear masks, the support rail structure may comprise a rear mask rest which provides support for the rear mask frame and/or the head support. Further, it is conceivable that the rear mask rest allows a rear mask frame and/or a head support to be snap-fitted to the support rail structure which will avoid that the head support or the rear mask frame is detached from the support rail structure unintentionally. The rear mask rest may be formed by a plurality of protrusions that may extend from the lateral sections of the support rail structure in a media-lateral direction.

BRIEF DESCRIPTION OF DRAWINGS

In the following, the invention is described with reference to the enclosed figures which represent preferred embodiments of the invention. The scope of the invention is however not limited to the specific features disclosed in the figures, which show:

FIG. 1 a perspective view of the inventive head immobilization system;

FIG. 2 a lateral view of the system shown in FIG. 1;

FIG. 3 a mask frame divided into sub-frames;

FIG. 4 the immobilization system of FIG. 1 with a head support and a posterior mask sheet installed.

DETAILED DESCRIPTION

The embodiment shown in FIG. 1 comprises four pins 7, two on each lateral side of the support rail structure 1 which is formed by a single, three-dimensionally formed and unsupported rail that is coupled to the patient rest 2 exclusively on both of its ends. The pins 7 serve as a guidance when the mask frame 3 is moved towards and connected to the support rail structure 1. Each one of the pins 7 has a saw-toothing 10 with a defined distance between the teeth. The teeth feature a horizontal upper side, wherein the lower side is beveled.

In the shown embodiment, the mask frame 3 (the mask 4 attached thereto is not shown) comprises two lateral rails, each one of the rails having two pin-receptions 8 which fit around the corresponding pins 7. Each one of the rails comprises a release mechanism 12 having a double-lever that is connected to the rail via two film-joints. It becomes apparent from FIG. 1 that pushing the "ring-shaped" grasping sections in the middle of each rail together will cause the double-lever to bend, with each end of the lever being rotated around the corresponding film-joint. Consequently, both ends of the double-lever that extend beyond the film-joints are deflected in an opposite direction. Each one of the lever-ends features a saw-toothing 11 within a pin-reception 8, that interlocks the saw-toothing 10 on the pins 7.

FIG. 1 shows an unactuated state of the release mechanism 12, with the spring loaded double-lever remaining in a neutral position which will allow the rails of the mask frame 3 to be pushed down over the pins 7 since each end of the double-levers will be deflected in a ratchet-like manner as the saw-toothings 10, 11 slide against each other. Moving the mask frame 3 upwards again, away from the support rail structure 1 is, however, prevented by the interlocking saw-toothings 10, 11 that are held against each other by the elastic double-lever.

To offer more flexibility when installing the mask frame 3 onto the support rail structure 1, especially during the mask molding process, the interfaces 5, 6 of the support rail structure 1 and the mask frame 3 are designed in a way that the receptacles 8 can be put over the pins 7 from an angular position (shown in FIG. 2). This makes it easy to mold the mask around the patient's chin first, and simultaneously inserting the caudal pins 7 (shown on the left in FIGS. 1 and 2) into the corresponding pin-receptions 8. For doing so, these pins 7 feature guidance protrusions 13 that enter into corresponding notches 14 of the caudal pin-receptions 8. The notches 14 prevent the mask frame 3 from moving in a cranial-caudal direction and provide guidance during the downward movement of the mask frame 3.

Subsequently, the mask frame 3 can be rotated such that the cranial pins 7 enter the corresponding pin-receptions 8, as well, and the mask frame 3 can be pushed down onto the support rail structure 1 in a translatory movement with the rails extending parallel to the support rail structure 1.

For removing the mask frame 3 from the support rail structure 1 again, the release-mechanism 12 is activated by pressing together the ring-shaped grasping sections in the middle of each rail, which will cause the saw-toothings 11 to move away from the corresponding saw-toothings 10. The mask frame 3 can now be moved upwards and released from the support rail structure 1.

The embodiment shown in FIGS. 1 and 2 further has an adjustable stop-mechanism 15. When the mask frame 3 is put over the pins 7, the saw-toothings 10, 11 interlock with each other automatically at the "highest" position. The saw-toothings 10, 11 together with the spring-loaded release-mechanism 12 allow to move the mask frame 3 further downwards by continuously pressing it down onto the support rail structure 1. This provides a self-adjustment of the upper mask sheet 4 (shown in FIG. 4) to the patient's anatomy in subsequent steps. The step distance is defined by the size of the teeth of the saw-toothings 10, 11, which is 1 mm for the embodiment shown in FIGS. 1 and 2.

In order to increase the distance between the upper mask 4 and the rear mask/head support 23 (shown in FIG. 4), the grasping sections of the release-mechanism 12 are pressed together and the mask frame 3 is moved upwards until the desired position is reached. As soon as the grasping sections are released, the saw-toothings 10 and 11 interlock again.

In the following, the adjustable stop-mechanism 15 is described, by which the minimum distance between the upper mask 4 and the rear mask/head support 23 can be adjustably defined.

The stop-mechanism 15 comprises three sections 16, each section 16 having four stepped locating surfaces 17. The sections 16 of each rail are connected to a common member that can slide along the lateral sections of the support rail structure 1, and with respect to the pins 7 in a cranial-caudal direction. An adjustment wheel 18 that is rotatably held with respect to the support rail structure 1 and that is connected to the common member via a rack and pinion drive 19 allows to adjust the positon of the sections 16 with respect to the pins 7 and therefore also with respect to the mask frame 3 that slides over the pins 7.

As can be seen in FIGS. 1 and 2, the minimum possible distance by which the mask frame 3 can be pushed down onto the support rail structure 1 decreases with the sections 16 being moved in a caudal direction, since locating surfaces of the mask frame 3 (defined by three pins provided on the bottom side of the mask frame 3) will come into contact with the corresponding locating surfaces 17 only in a predetermined position with respect to the pins 7.

The stop-mechanism 15 allows to pre-adjust the amount by which the upper mask sheet 4 can be pressed onto the patient's face not only during the molding process, but also at a later stage when the patient's head has to immobilized in a predefined position.

As already indicated above, the mask frame 3 can be adapted to allow molding of one or more mask sheets. For example, if the upper mask consists of only one mask sheet 4, the mask frame 3 can be attached to the support rail structure 1 in a single step. If however, the upper mask consists of two or more mask sheets 4a, 4b, the mask sheet 4a closest to the patient's skin is molded first, while a first sub-frame 3a is connected to the support rail structure 1 in the manner described above. A further mask sheet 4b which is molded afterwards and thereby will come to rest above the first mask sheet 4a is coupled to a second sub-frame 3b that in turn is coupleable to the first sub-frame 3a by a plurality of snap-in fasteners 20 as shown in FIG. 3. Each one of the snap-in fasteners 20 comprises at least one barb that will prevent the second sub-frame 3b to be released from the first sub-frame 3a again. Once the two sub-frames 3a and 3b are fixedly connected, they can be handled as one unit. They can be attached to or removed from the support rail structure 1 in a manner that has been already described further above in connection with the single frame 3.

FIG. 4 further shows an undeformable head support 23, which may be supplemented or replaced by deformable mask sheet 22. Both, the head support 23 and the rear mask sheet 22 may comprise a frame structure (not shown) which may be snap-fitted to the protrusions 24 (shown in FIG. 1) and may therefore be detachably connected to the support rail structure 1.

Any of the mask sheets 4, 4a, 4b can be connected to the corresponding mask frame 3, 3a, 3b by being inserted and glued into slots of the mask frame 3, 3a, 3b (shown in FIGS. 1 and 2). Alternatively, the mask sheets 4, 4a, 4b can be laser-welded to the corresponding mask frames 3, 3a, 3b.

In the following, possible configurations for the overall mask fixation system are described:

Mask Configuration 1:
  Head support 23 (may be removed after mask molding)
  Rear mask 22 (custom made to fit patient)
  Middle mask 4a (custom made to fit patient)
  Top mask 4b (custom made to fit patient)
Options for 1:
  Middle and top mask sheet 4a, 4b may come rigidly prefixed together by means of lateral rails of mask frames 3a, 3b
  Instead of a middle and a top mask 4a, 4b the upper mask consist of just a top mask 4 (no middle mask 4a in this configuration)
  Additional moldable nose bridge fixation, that is molded to the patient's nose bridge out of thermoplastic pallet material and located between the patient and the middle and/or top mask 4a, 4b (custom made to fit patient)
  Optionally eye openings in upper mask
  Optionally face opening in upper mask
  Optionally forehead opening in upper mask Mask Configuration 2:
  Head support 23 (cannot be removed after mask molding)
  Upper mask (custom made to fit patient), attached to mask frame
Options for 2:
  Additional middle mask 4a
  Additional moldable nose bridge fixation, that is molded to the patient's nose bridge out of thermoplastic pallet material and located between the patient and the middle and/or top mask 4a, 4b (custom made to fit patient)
  Optionally eye openings in upper mask
  Optionally face opening in upper mask
  Optionally forehead opening in upper mask The patient rest 2 (shown in FIGS. 1, 2 and 4) is typically secured to a treatment table by means of mounting brackets (not shown) which may position the patient rest 2 to the treatment table's indexing system in an interlocking manner for a defined and reproducible position. The patient rest 2 may be attached to the treatment table in a force-locking manner, as well as by brackets that embrace the table top and can be locked by a fastener. The patient rest 2 has a material minimized design that reduces it's effects on attenuation and dose build-up when the radiation beam has to pass the patient rest 2. The patient rests 2 support rail structure 1 incorporate the mask fixation and connection points for the upper and lower mask shell, the rear head support 23 and the height adjustment unit 15. To minimize the collision risk with a linear accelerator, the support rail structure 1 of the patient rest 2 is located as close as possible to the longitudinal middle axis of the patient's head. The cranial bar extending in a medial-lateral direction and connecting the lateral sections of the support rail structure 1 is located as close as possible to the head, following the head's anatomy.

In the following, preferred workflows in the context of the inventive head immobilization system are described:

Workflow Mask Molding
  Place the patent rest 2 onto the CT-tabletop or treatment tabletop and fasten it
  Attach the head support 23 to the support rail structure 1 by hanging it onto the lateral protrusions 24
  Heat the thermoplastic material of the masks to the molding temperature
  (Optional) attach the posterior mask together with frame 22 to the support rail structure 1 by clipping it into the lateral protrusions 24

(Optional) mold the posterior mask to the patient's back of the head

Place the patient into the posterior mask, respectively the head support 23

Adjust the two lateral stop-mechanisms 15 to the dedicated vertical home position Attach mask 4*a* together with frame 3*a* to the support rail structure 1 by clipping it to the spring loaded catch-mechanism 9. The mask 4*a* will be secured in the dedicated vertical position automatically.

(Optional) mold a nose bridge to the patients nose using the thermoplastic material (Optional) attach mask 4*b* together with frame 3*b* to the mask 4*a* and frame 3*a* by clipping together the sub-frames 3*a* and 3*b*. The middle mask 4*a* and the upper mask 4*b* will be permanently joint.

Work-Flow Patient Fixation

Place the patient rest 2 onto the treatment tabletop and fasten it (Optional) attach the head support 23 to the support rail structure 1 by hanging it into the lateral protrusions 24

(Optional) attach the posterior mask together with frame 22 to the support rail structure 1 by clipping it into the lateral protrusions 24

Place the patient into the posterior mask

Adjust the two lateral stop-mechanisms 15 to the dedicated vertical home position Attach mask 4*a* together with frame 3*a* and mask 4*b* together with frame 3*b* (optionally just mask 4*a* with frame 3*a*) onto the patients head by clipping it into the spring loaded catch-mechanism 9. The mask(s) 4*a*/4*b* will be secured in the dedicated vertical position automatically.

If the mask(s) 4*a*/4*b* is/are too tight or too loose, adjust the tightness with the stop-mechanisms 15 to tighten/loosen mask(s) 4*a*/4*b* by enlarging or reducing the distance between the rear head mask/head support 23 and the upper mask(s) 4*a*/4*b*.

To loosen the mask(s) 4*a*/4*b*, actuate the release-mechanism 12 and lift it, until the dedicated vertical position is reached. Adjust the sections 16 of the stop-mechanisms 15 to the suitable position.

To tighten the mask(s) 4*a*/4*b*, adjust the sections 16 of the stop-mechanisms 15 to the suitable lower position. Push the mask(s) 4*a*/4*b* down until the dedicated vertical position is reached.

To remove the mask(s) 4*a*/4*b* after treatment activate the release-mechanism 12 and lift the mask(s) 4*a*/4*b*. Remove the rear head mask and the head support 23 by lifting them up.

The invention claimed is:

1. A mask system for immobilizing a patient's head relative to a support rail structure of a head immobilization system, comprising:
   at least one deformable patient mask sheet; and,
   a mask frame coupled to the at least one deformable patient mask sheet, the mask frame including:
      plural interface sections, each interface section including a releasable pin receiver having a sawtooth catch structure on a surface, wherein each releasable pin receiver receives a corresponding one of at least one pin extending from the support rail structure of the head immobilization system, and wherein the sawtooth catch structure engages a corresponding saw tooth structure on the pin to allow the pin to be pushed progressively further into the releasable pin receiver, but to prevent removal of the pin from the pin receiver unless released; and
      a release mechanism including grasping sections that, when pressed, cause the sawtooth catch structure of each releasable pin receiver to release from engagement with the corresponding saw tooth structure of the corresponding one of the at least one pin.

2. The system of claim 1, wherein the at least one deformable patient mask sheet includes plural deformable patient mask sheets.

3. The system of claim 2, wherein one mask sheet of the plural deformable patient mask sheets is configured to be molded to the patient's nose bridge.

4. The system of claim 1, wherein the grasping sections are tabs.

5. The system of claim 4, wherein the tabs are ring-shape.

6. The system of claim 1, wherein the at least one deformable patient mask sheet is a thermoplastic sheet.

7. The system of claim 1, wherein the at least one deformable patient mask sheet includes eye holes.

8. The system of claim 1, wherein the at least one deformable patient mask sheet includes a rear patient mask sheet and a top patient mask sheet.

9. The system of claim 1, wherein the at least one deformable patient mask sheet includes a rear patient mask sheet, a middle patient mask sheet, and a front patient mask sheet.

10. The system of claim 1, wherein each releasable pin receiver is spring biased into closed position retaining the corresponding at least one pin.

11. A system for immobilizing a patient's head relative to a head immobilization system, comprising:
    a deformable plastic sheet; and
    a mask frame, the mask frame including:
       an engagement system for engaging a portion of the plastic sheet and plural interface sections, each interface section including a releasable pin receiver having a sawtooth catch structure on a surface, wherein each releasable pin receiver receives a corresponding one of at least one pin extending from a support rail structure and wherein the saw tooth catch structure engages a corresponding saw toothed structure of the pin to allow the pin to be pushed progressively further into the releasable pin receiver, but to prevent removal of the pin from the pin receiver unless released; and
       a release mechanism including grasping sections that, when pressed, cause the sawtooth catch structure of each releasable pin receiver to release from engagement with the saw toothed structure of the corresponding one of the at least one pin.

12. The system of claim 11, wherein the mask frame includes two lateral rails, each including the plural interface sections.

13. The system of claim 11 including an adjustment mechanism that varies a distance between the support rail and a lateral rail of the mask frame.

14. A radiation therapy system, comprising:
    a mask system, including:
       at least one deformable patient mask sheet; and
       plural mask frames, each mask frame including:
          an engagement system for engaging a portion of the at least one deformable patient mask sheet and plural interface sections, each interface section including a releasable pin receiver having a sawtooth catch structure on a surface; wherein each sawtooth catch structure receives a corresponding one of at least one pin extending from a pair of support rails and engages a corresponding saw tooth structure on the corresponding one of the at least one pin to allow the pin to be pushed progressively further into the releasable pin receiver, but to prevent removal of the pin from the releasable pin receiver unless released; and a release mechanism including grasping sections that, when pressed, cause the sawtooth catch structure of each releasable pin receiver to release from engagement with the corresponding saw tooth structure on the corresponding one of the at least one pin.

* * * * *